(12) United States Patent
Heikenfeld et al.

(10) Patent No.: US 11,931,144 B2
(45) Date of Patent: *Mar. 19, 2024

(54) SWEAT RATE MEASUREMENT DEVICES

(71) Applicant: University Of Cincinnati, Cincinnati, OH (US)

(72) Inventors: Jason Charles Heikenfeld, Cincinnati, OH (US); Michelle D. Hoffman, Wyoming, OH (US); Mikel Larson, Cincinnati, OH (US); Nicholas Bailey, Cincinnati, OH (US); Andrew Beckman, Loveland, OH (US); Adam Hauke, New Richmond, OH (US)

(73) Assignee: University Of Cincinnati, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/820,305

(22) Filed: Aug. 17, 2022

(65) Prior Publication Data

US 2022/0409104 A1 Dec. 29, 2022

Related U.S. Application Data

(63) Continuation of application No. 16/954,226, filed as application No. PCT/US2018/066257 on Dec. 18, 2018, now Pat. No. 11,445,943.

(Continued)

(51) Int. Cl.
*A61B 5/145* (2006.01)
*A61B 5/00* (2006.01)
(Continued)

(52) U.S. Cl.
CPC ........ *A61B 5/14517* (2013.01); *A61B 5/6801* (2013.01); *A61B 5/7203* (2013.01);
(Continued)

(58) Field of Classification Search
CPC . A61B 5/14517; A61B 5/1477; A61B 5/4266; A61B 10/0064; A61B 5/14514;
(Continued)

(56) References Cited

U.S. PATENT DOCUMENTS

2004/0249253 A1* 12/2004 Racchini .......... A61B 5/150022
600/347
2006/0257993 A1* 11/2006 McDevitt .......... G01N 21/6428
435/287.2

(Continued)

FOREIGN PATENT DOCUMENTS

EP 3242112 A1 * 11/2017 .......... A61B 5/4266
EP 3242112 A1 11/2017
(Continued)

OTHER PUBLICATIONS

Elwenspoek, M., "Thermal Flow Micro Sensors" CAS '99 Proceedings. 1999 International Semiconductor Conference (Cat. No. 99TH8389), p. 423-435 (Year: 1999).*

(Continued)

*Primary Examiner* — Navin Natnithithadha
*Assistant Examiner* — Alice Ling Zou
(74) *Attorney, Agent, or Firm* — Wood Herron & Evans LLP

(57) ABSTRACT

Devices and methods are described herein for directly and accurately measuring sweat flow rates using miniaturized thermal flow rate sensors. The devices (100, 200, 300, 400, 500, 600, 700, 800, 900, 1000, 1100, 1200, 1300, 1400, 1500) include the flow rate sensors (220, 320, 420, 520, 620, 720, 820, 920, 1020, 1120, 1220, 1320, 1420) in or adjacent to a microfluidic component (230, 330, 430, 530, 630, 730, 830, 930, 1030, 1130, 1230, 1330, 1430, 1530) of a wearable sweat sensing device. The devices and methods optimize the sensitivity of the flow rate sensors, while minimizing the (Continued)

presence of noise, in order to accurately and directly measure sweat flow rates.

19 Claims, 7 Drawing Sheets

Related U.S. Application Data

(60) Provisional application No. 62/599,819, filed on Dec. 18, 2017.

(51) Int. Cl.
*G01F 1/684* (2006.01)
*G01F 5/00* (2006.01)

(52) U.S. Cl.
CPC .......... *G01F 1/6842* (2013.01); *G01F 1/6845* (2013.01); *G01F 5/00* (2013.01); *A61B 2562/0271* (2013.01); *A61B 2562/028* (2013.01)

(58) Field of Classification Search
CPC ............ A61B 5/14521; A61B 5/14532; A61B 5/14546; A61B 5/1486; A61B 5/1491; A61B 5/6801; A61B 5/6831–6833
See application file for complete search history.

(56) References Cited

U.S. PATENT DOCUMENTS

| | | | |
|---|---|---|---|
| 2009/0182216 A1* | 7/2009 | Roushey, III | ........ A61B 5/4266 600/364 |
| 2018/0020981 A1 | 1/2018 | Heikenfeld | |

FOREIGN PATENT DOCUMENTS

| | | | |
|---|---|---|---|
| WO | 2016197116 A1 | 12/2016 | |
| WO | WO-2016197116 A1 * | 12/2016 | ......... A61B 10/0012 |
| WO | 2017070640 A1 | 4/2017 | |
| WO | WO-2017070640 A1 * | 4/2017 | ......... A61B 10/0012 |
| WO | WO-2017218878 A1 * | 12/2017 | ........... A61B 5/0059 |

OTHER PUBLICATIONS

International Search Report and Written Opinion in International Patent Application No. PCT/US2018/066257, dated Feb. 26, 2019, 13 pgs.

Sonner, Z. et al., "The microfluidics of the eccrine sweat gland, including biomarker partitioning, transport, and biosensing implications," Biomicrofluidics 9, 031301 (2015), 20 pgs.

* cited by examiner

SWEAT RATE MEASUREMENT DEVICES

CROSS-REFERENCE TO RELATED APPLICATIONS

This application is a continuation of U.S. patent application Ser. No. 16/954,226, filed on Jun. 16, 2020, which is a national stage application under 35 U.S.C. § 371 of International Application No. PCT/US2018/066257, filed on Dec. 18, 2018, which claims priority to, and the benefit of the filing date of, U.S. Provisional Application No. 62/599,819, filed on Dec. 18, 2017, the disclosures of which are incorporated herein by reference in their entireties.

BACKGROUND OF THE INVENTION

Sweat sensing technologies have enormous potential for applications ranging from athletics, to neonatology, pharmacological monitoring, and personal digital health. The available applications for sweat sensing technologies are so numerous because sweat contains many of the same biomarkers, chemicals, and solutes that are carried in blood. The presence of these biomarkers, chemicals and solutes in sweat can provide significant information for non-invasively diagnosing ailments, determining health status, diagnosing toxins, measuring performance, and other physiological attributes, even in advance of any physical sign. Furthermore, sweat itself, and the action of sweating, as well as other parameters, attributes, solutes, or features on or near skin or beneath the skin, can be measured to further reveal physiological information.

Among the biofluids used for physiological monitoring (e.g., blood, urine, saliva, tears), sweat has arguably the least predictable sampling rate in the absence of technological solutions. An excellent summary of the challenges in sweat sampling is provided by Sonner, et al. in the 2015 article titled "The microfluidics of the eccrine sweat gland, including biomarker partitioning, transport, and biosensing implications," Biomicrofluidics 9, 031301, incorporated by reference herein in its entirety. With proper application of technology, however, sweat can be made to outperform other non-invasive or less invasive biofluids in predictable sampling. In particular, sweat sensing devices hold tremendous promise for use in workplace safety, athletic, military, and clinical diagnostic settings.

An important aspect of predictable sweat sampling is providing decision support that is informative at the level of the individual user. A sweat sensing device worn on the skin and connected to a computer network via a reader device, such as a smart phone or other portable or stationary device, can aid in recognition of the physiological state of the wearer and relay crucial data that can inform decision-making about medical treatment, physical training, safety requirements, and other applications. Sweat sensors have the potential to continuously monitor one or more aspects of an individual's physiological state. Relevant information of the wearer's physiological state can then be communicated to a computer network and compared to threshold readings. From this comparison, notification messages can be generated and communicated to the individual, a caregiver, a work supervisor, or other device user.

One challenge with sweat sensing technologies is accurately measuring sweat generation rates. Traditionally, the loss of water and electrolytes through sweating has been determined through skin impedance measurements. Skin impedance alone, however, only provides a relative measure of sweat generation rate. The direct measurement of sweat generation rates has remained a challenge because sweat flow rates are at the very low end of what conventional flow rate sensors can measure. Furthermore, placement of conventional flow rate sensors on the body can cause numerous confounding factors.

Recently, miniaturized flow rate sensors have been developed that enable flow rates as low as a few microliters per minute to be accurately measured. The miniaturized size of these sensors allows for use in a sweat sensing system. However, the small size and low flow rates make the sensors subject to sensitivity issues and inaccuracies due to noise from a number of causes including: differential fluid pressures in the device, motion artifacts, movement of the device on a wearer's body, or movement of the body itself. Noise can inject errors into the flow rate measurements, thereby compromising the accuracy of the sweat sensing system. Additionally, the low flow rate of sweat can negatively impact the sensitivity of the sensor.

Accordingly, it is desirable to have devices and methods for incorporating miniaturized flow rate sensors into sweat sensing technologies. In particular, it is desirable to have devices and methods for directly and accurately measuring sweat flow rates using one or more flow rate sensors in a microfluidic component of a sweat sensing device. It is desirable that these devices and methods account for sensor sensitivity and noise to accurately measure sweat flow rates.

SUMMARY OF THE INVENTION

Many of the drawbacks and limitations stated above can be resolved by creating novel and advanced interplays of chemicals, materials, sensors, electronics, microfluidics, algorithms, computing, software, systems, and other features or designs, in a manner that affordably, effectively, conveniently, intelligently, or reliably brings sensing technology into proximity with sweat as it is generated on the surface of the skin.

The devices and methods described herein directly and accurately measure sweat flow rates using miniaturized thermal flow rate sensors. The devices include the flow rate sensors in or adjacent to a microfluidic component of a wearable sweat sensing device. The devices and methods optimize the sensitivity of the flow rate sensors, while minimizing the presence of noise, in order to accurately and directly measure sweat flow rates. In a first embodiment, a sweat sensing device capable of measuring sweat flow rate includes at least one flow rate sensor for measuring a sweat flow rate and at least one analyte sensor for measuring a characteristic of an analyte in sweat. The device also includes a microfluidic component for conveying at least one sweat sample into fluid communication with the at least one flow rate sensor and the at least one analyte sensor. At least a portion of the microfluidic component comprises a volume-reduced pathway adjacent to the flow rate sensor.

BRIEF DESCRIPTION OF THE DRAWINGS

The present disclosure will be further appreciated in light of the accompanying drawing figures in which.

DEFINITIONS

Figure 1:
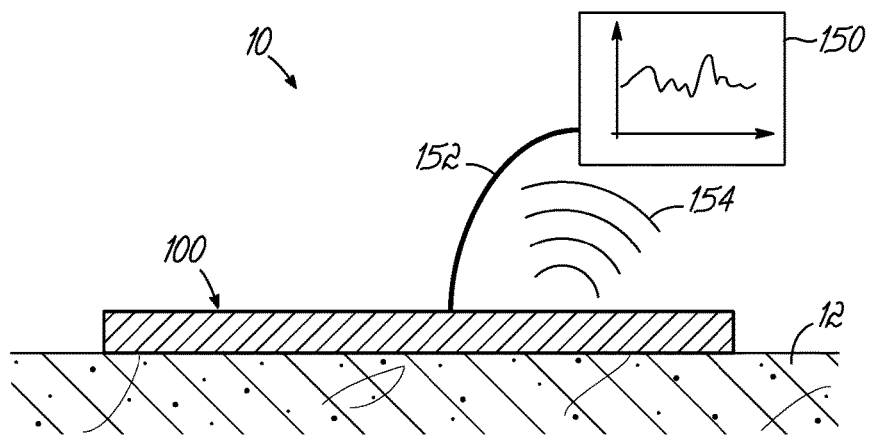
FIG. 1 is a schematic representation of an exemplary sweat sensing system.

Before continuing with a detailed description of the exemplary embodiments, a variety of definitions should be made, these definitions gaining further appreciation and scope in the detailed description and embodiments of the present disclosure.

As used herein, "sweat" means a biofluid that is primarily sweat, such as eccrine or apocrine sweat, and may also include mixtures of biofluids such as sweat and blood, or sweat and interstitial fluid, so long as advective transport of the biofluid mixtures (e.g., flow) is primarily driven by sweat.

"Continuous monitoring" means the capability of a device to provide at least one measurement of sweat determined by a continuous or multiple collection and sensing of that measurement or to provide a plurality of measurements of sweat over time.

"Sweat sensor" means any type of sensor that measures a state, presence, flow rate, solute concentration, solute presence, in absolute, relative, trending, or other ways in sweat.

Sweat sensors can include, for example, potentiometric, amperometric, impedance, optical, mechanical, antibody, peptide, aptamer, or other means known by those skilled in the art of sensing or biosensing.

"Sweat rate" means the rate at which sweat is generated per unit area of skin. For example, 100 active glands/cm$^2$, in an area of 1 cm$^2$, and a sweat generation rate of 1 nL/min/gland would produce a sweat rate of 100 nL/min/cm$^2$. Knowing the exact sweat generation rate per gland is not required, but knowing the flow rate (volume/time) and area generating that flow rate can be used to determine the sweat rate according to methods described herein.

"Sweat generation rate" is the rate at which sweat is generated by the sweat glands themselves. Sweat generation rate is typically measured by the flow rate from each gland in nL/min/gland. In some cases, the measurement is then multiplied by the number of sweat glands from which the sweat is being sampled.

"Analyte" means a substance, molecule, ion, or other material that is measured by a sweat sensing device.

"Measured" can imply an exact or precise quantitative measurement and can include broader meanings such as, for example, measuring a relative amount of change of something. Measured can also imply a binary measurement, such as 'yes' or 'no' type measurements.

"Chronological assurance" means the sampling rate or sampling interval that assures measurement(s) of analytes in sweat in terms of the rate at which measurements can be made of new sweat analytes emerging from the body. Chronological assurance may also include a determination of the effect of sensor function, potential contamination with previously generated analytes, other fluids, or other measurement contamination sources for the measurement(s). Chronological assurance may have an offset for time delays in the body (e.g., a well-known 5 to 30-minute lag time between analytes in blood emerging in interstitial fluid), but the resulting sampling interval (defined below) is independent of lag time, and furthermore, this lag time is inside the body, and therefore, for chronological assurance as defined above and interpreted herein, this lag time does not apply.

"Analyte-specific sensor" means a sensor specific to an analyte which performs specific chemical recognition of the analyte's presence or concentration (e.g., ion-selective electrodes, enzymatic sensors, electro-chemical aptamer-based sensors, etc.). For example, sensors that sense impedance or conductance of a fluid, such as sweat, are excluded from the definition of "analyte-specific sensor" because sensing impedance or conductance merges measurements of all ions in sweat (i.e., the sensor is not chemically selective; it provides an indirect measurement). Sensors can also be optical, mechanical, or use other physical/chemical methods which are specific to a single analyte. Further, multiple sensors can each be specific to one of multiple analytes.

"Sweat sensor data" means all of the information collected by sweat system sensor(s) and communicated via the system to a user or a data aggregation location.

"Sweat conductivity" means measurements of the electrical conductivity of sweat. Sweat conductivity serves as a means of estimating $Cl^-$ content, since $Cl^-$ represents the dominant anion in sweat. However, conductivity does not precisely correlate to $Cl^-$ levels, because lactate and bicarbonate also make significant contributions to sweat conductivity. A sweat sensing device as described herein would measure sweat conductivity with an electrode.

"Microfluidic components" are channels in polymer, textiles, paper, glass, or other components known in the art of microfluidics for guiding movement of a fluid or at least partial containment of a fluid.

"Advective transport" is a transport mechanism of a substance or conserved property by a fluid due to the fluid's bulk motion.

"Diffusion" is the net movement of a substance from a region of high concentration to a region of low concentration. This is also referred to as the movement of a substance down a concentration gradient.

"Volume-reduced pathway" is a sweat volume that has been reduced by addition of a material, device, layer, or other body-foreign substance, which therefore increases the sweat sampling interval for a given sweat generation rate. This term can also be used interchangeably in some cases with a "reduced sweat pathway", which is a pathway between eccrine sweat glands and sensors that is reduced in terms of volume or in terms of surfaces wetted by sweat along the pathway. Volume reduced pathways or reduced sweat pathways include those created by sealing the surface of skin, because skin can absorb or exchange water and solutes in sweat which could increase the sweat sampling interval and/or cause contamination, which can also alter the accuracy or duration of the sweat sampling interval.

DETAILED DESCRIPTION OF THE INVENTION

The embodiments described herein will be primarily, but not entirely, limited to wearable sweat sensing devices, and methods or sub-methods using wearable sweat sensing devices. The disclosed embodiments may be practiced using any type of wearable sweat sensing device that measures sweat, sweat generation rate, sweat chronological assurance, sweat solutes, solutes that transfer into sweat from skin, a property of or things on the surface of skin, or properties or things beneath the skin. A sweat sensing device as discussed herein can take on many forms, including patches, bands, straps, portions of clothing or equipment, or any suitable mechanism that reliably brings sweat stimulating, sweat collecting, and/or sweat sensing technology into intimate proximity with sweat as it is generated.

Certain embodiments of the disclosed invention show sensors as simple individual elements. It is understood that many sensors require features which are not captured in the description herein. Sensors are preferably electrical in nature, but may also include optical, chemical, mechanical, or other known biosensing mechanisms. Sensors can be in duplicate, triplicate, or more, to provide improved data and readings. Certain embodiments of the disclosed invention show sub-components of what would be sensing devices with more subcomponents, which are known (i.e. battery, antenna, adhesive), needed for use of the device in various applications. For purposes of brevity and focus on inventive aspects, such components are not explicitly shown in the diagrams or described in the embodiments of the disclosed invention. Additionally, descriptions of elements in the alternative may be considered as distinct alternative embodiments that are exclusive of one another. Further, the specific embodiments have distinct combinations of elements, but these elements may be incorporated across embodiments shown. Likewise, the advantages disclosed for an embodiment may apply equally to other embodiments.

A number of different embodiments are described herein for integrating a microfluidic flow rate sensor in a sweat sensing system. In these embodiments, a microfluidic flow rate sensor measures sweat flow rate without negatively impacting analyte sensor functionality. These embodiments include improving the sensitivity of the flow rate sensor by minimizing the dead volume of the fluid coupling component adjacent the sensor. In addition to increasing sensitivity, the embodiments described herein reduce the effect of system noise on the flow rate sensor measurements.

Turning now to FIG. 1, which depicts a representative sweat sensing system 10 to which the present disclosure applies. Sweat sensing system 10 includes a sweat sensing device 100 capable of measuring sweat rate. Device 100 may be placed near or directly on skin 12. The sweat sensing device 100 may be fluidically connected to skin 12, or regions near the skin, through microfluidics or other suitable techniques. Device 100 is in wired communication 152 or wireless communication 154 with a reader device 150, which can be, for example, a smart phone or other portable electronic device or, for some embodiments, the sensing device 100 and reader device 150 can be combined. Communication 152 or 154 may be continuous, or may occur periodically, at set or variable time periods, or as a simple, one-time data download from the sensing device 100 to the reader device 150 once the sensing device 100 has completed sweat measurements.

Figure 2:
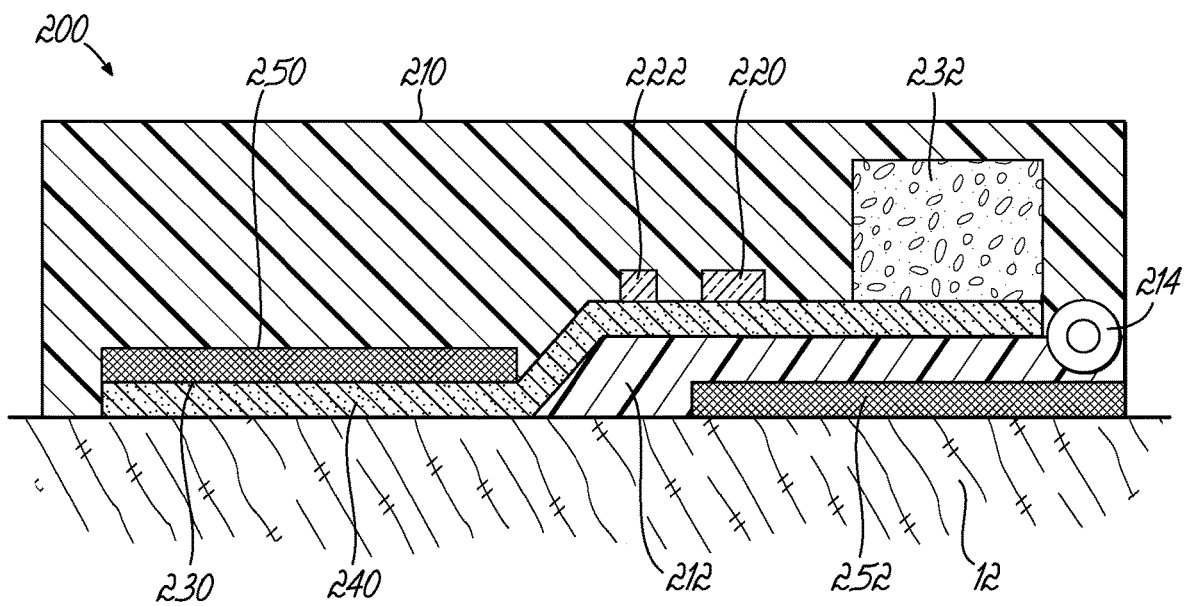
FIG. 2 is a cross-sectional view of at least a portion of a wearable device or patch for sweat biosensing.

With reference to FIG. 2, in an embodiment of the disclosed invention, a device 200 capable of measuring sweat rate is shown placed on skin 12. The device 200 includes a housing 210 coupled to a latch 212 via a hinge 214. Suitable materials for each of the housing 210 and latch 212 include, without limitation, polymers, such as nylon, silicone, rubber, etc. The device 200 further includes a microfluidic component 230, such as a channel formed in the housing 210, that fluidically couples the skin 12 to a flow rate sensor 220, and a secondary sensor 222. An optional sweat pump 232 may also be included in the device 200. In the embodiments described herein, sweat can be conveyed through a microfluidic component of a sensing device by any number of different techniques including wicking, diffusion, capillary action, advective transport, and hydraulic pressure from a sweat gland, among others. In the embodiment shown in FIG. 2, microfluidic component 230 includes a wicking component 240 for at least partially transporting sweat in the device 200. The wicking component may be made of, for example, paper or a woven or non-woven textile. The pump 232 also includes a wicking component, such as a sponge or hydrogel. The pump 232 may allow for continuous wicking and flow of newly generated sweat from skin 12 to the pump 232, and may have a capacity of, for example, greater than 1 μL, or from 1 μL to 1 mL, or greater than 1 mL. The wicking component 240 and pump 232 may be permanent, semi-disposable (i.e., reusable for a limited number of uses), or fully disposable (i.e., dispose after single use) by placement into the device and being held in place by latch 212. The wicking component 240 and pump 232 may be made of reusable or disposable materials, which may be replaced as needed using the latch 212.

In the embodiments described herein, flow rate sensor refers to any type of microfluidic flow rate sensor. In an embodiment, the flow rate sensor is a thermal flow rate sensor that uses a temperature differential to calculate a fluid flow rate. Suitable thermal flow rate sensors for application in the devices 100, 200, 300, 400, 500, 600, 700, 1000, 1100, 1200, 1400 described herein include, without limitation, those manufactured by Sensirion AG Switzerland. In addition to the Sensirion sensors, it is envisioned that other thermal flow rate sensors will also be applicable to the disclosed embodiments. Furthermore, other types of microfluidic flow rate sensors may also be used in the embodiments disclosed herein including, without limitation, optical, chemical, or electro-mechanical sensors. The flow rate sensor 220 is at least adjacent to, and may be located within, the microfluidic component 230, so as to be in contact with sweat as the sweat is transported through the component. In an embodiment, the flow rate sensor is capable of measuring a flow rate that ranges from 10 mL/min to 100 mL/minute. In another embodiment, the flow rate sensor is capable of measuring a flow rate that ranges from 10 µL/min to 100 µL/min.

The device 200 may also include an electrode 250 (e.g., suitable electrodes may be stainless steel electrodes, carbon electrodes, etc.) and a counter-electrode 252. In the presence of sweat, wicking component 240 becomes fully wet with sweat, which creates an electrical connection between the electrode 250 and the skin 12. As a result, electrodes 250, 252 can be used to measure skin impedance—a relative measure of sweat generation rate. The secondary sensor 222 may be, for example, an ion-selective electrode for sensing an analyte in sweat (e.g., Cl−) or a metal electrode that measures the electrical conductivity between the sensor 222 and the electrode 250, which is used to estimate Cl− concentration. Sweat conductivity and Cl− concentration are also indirect measurements of sweat rate. In an aspect of the disclosed invention, measurements of sweat rate by at least two of the sensors 220, 222, and electrodes 250, 252 are used together to obtain a more accurate or prolonged measurement of sweat generation rate.

With further reference to FIG. 2, several inventive aspects allow the device 200 to provide accuracy and precision in the measurement of sweat flow rates. First, the amount of sweat adjacent to sensor 220 is relatively constant to avoid measurement errors. With existing thermal flow rate sensors, measurable flow rates will typically range from 10's nL/min to 10's µL/min. For example, if the volume of fluid adjacent to the sensor changes by 10%, then the flow rate measurement could be erroneous by a similar amount (i.e., the measurement would be lower than the actual flow rate). To ensure a relatively constant measurement of flow rate, both the thickness of sweat (i.e., the sweat in the wicking component 240) adjacent to the sensor 220, and the percent wetting (filling) of the wicking component 240 adjacent to the sensor 220, must be as constant as possible, not changing by more than 5%, or changing between 5 and 10%, or changing not more than 10%, or changing between 5% and 30%, or changing not more than 30%. Second, the flow of sweat across the sensors 220, 222 should not reverse direction (i.e., towards the skin 12). Flow reversal for a thermal flow sensor can give erroneous readings; for example, a sweat sample may be measured a first time as it passes the sensor, a second time as the sample reverses direction backwards past the sensor, and then a third time as the sample moves forward again past the sensor towards the pump. If flow reversal does occur, software or electronics (not shown) can be used to recognize the flow reversal, and remove or correct erroneous readings. For example, the time period of change in sweat generation rate will be several minutes or slower (especially to reach a sweat generation rate of zero which could be 5-10 minutes or more), whereas flow reversals due to body movements would generally be faster (e.g., seconds, or less than a minute, in most cases). Thus, the change in sweat generation rate as determined by the flow rate sensor that is less than would be expected if the change occurred from the subject's actual sweat generation rate (e.g., less than 5 minutes or less than 1 minute or less than 30 seconds) then the detected change in flow rate may be noted as being due to flow reversal, and the erroneous reading may be corrected.

With further reference to FIG. 2, the device 200 may be configured to keep the wicking component 240 fully wetted with sweat during use. For example, the wicking component 240 may have the strongest wicking pressure of materials used in the device 200, including the pump 232, such that the material of wicking component 240 is always fully wetted with sweat during use. In an example, the material of wicking component 240 may be made of paper, and the pump 232 may be made of a highly porous sponge. Additionally, the device 200 will experience potential differential pressures of fluid flowing from the skin 12 into the wicking component 240 due to movement on skin, muscle contraction, etc. The wicking pressure of the pump 232 should be greater than these differential pressures such that flow reversal does not occur in the device 200. Other techniques to promote unidirectional flow are possible, as will be described in more detail below. With regard to a constant volume or thickness of the material of wicking component 240 adjacent to the sensor 220, several example configurations are as follows. In an embodiment, the wicking component 240 may be incompressible above the sensor 220 (e.g., a porous ceramic material). In another embodiment, the hinge 214 may be regulated in height with polymer stand-offs or spacers such that the thickness and/or volume of sweat in the wicking component 240 is precisely controlled, or such that the sensor 220 is not damaged by too much pressure against it. The wicking component 240 may also be a compressible material (e.g., cellulose or a hydrogel) embedded with rigid spacers such as incompressible balls (e.g., ceramic spheres made by 3M Corp.).

Figure 3A:
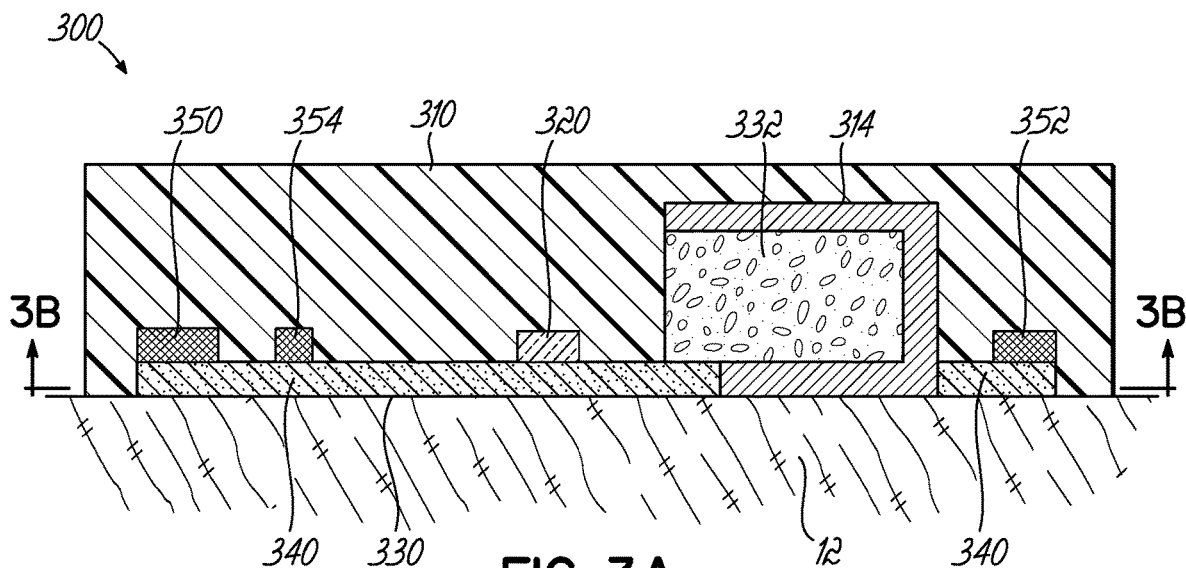
FIG. 3A is a cross-sectional view of at least a portion of a device for measuring sweat rate according to an embodiment of the disclosed invention.
Figure 3B:
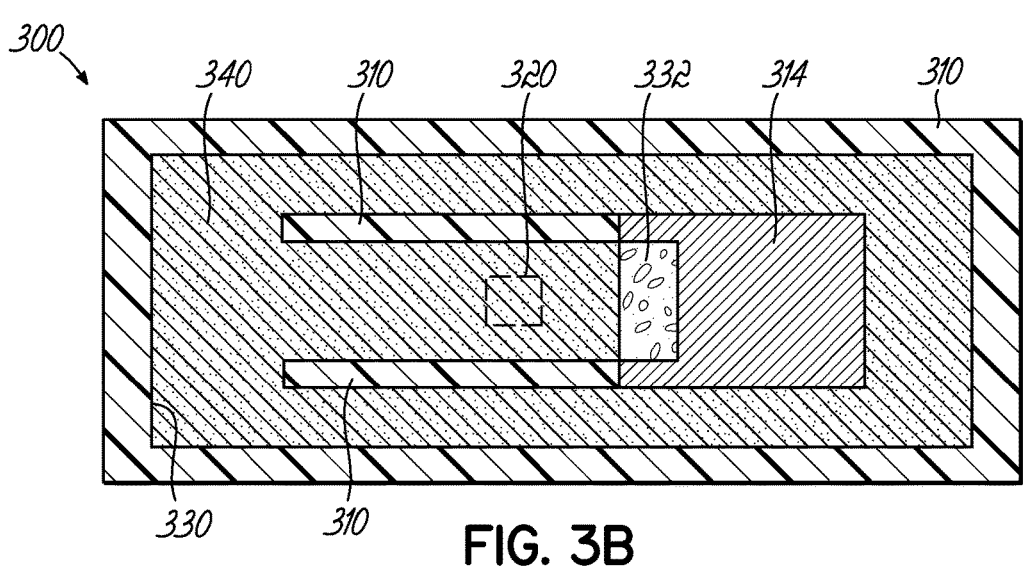
FIG. 3B is a plan view of the device of FIG. 3A viewed in the direction of arrows 390 in FIG. 3A.
Figure 3C:
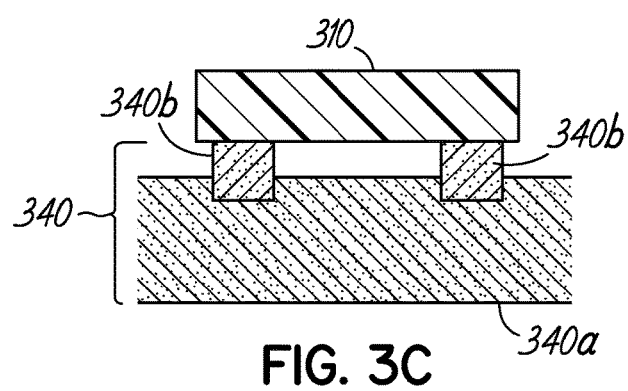
FIG. 3C is a cross-sectional view of a portion of a wicking or microfluidic material or component.

With reference to FIGS. 3A-3C, in an embodiment wherein like numerals refer to like features as shown in FIG. 2, a device 300 capable of measuring sweat rate is shown on skin 12. The device 300 includes a housing 310 and a microfluidic component 330 comprising a channel formed in the housing 310 that further includes a wicking component 340 or material at least partially disposed within, for transporting sweat from the skin 12 across a flow sensor 320 to a pump 332. A casing 314 at least partially surrounds the pump 332 and allows the pump 332 to be easily inserted and removed from the device 300, and/or blocks the direct wicking of sweat from the skin 12 into the pump 332. The casing 314 may be made of, for example, a polymer. The housing 310 and casing 314 may be made from the same type of material as different materials such as the materials previously described for housing 210 of the embodiment illustrated in FIG. 2. One or both of the electrodes 352, 354 may be used to measure sweat conductivity through a counter electrode such as electrode 350. FIG. 3B shows a plan view of the device 300 facing the skin 12, viewed in the direction of arrows 390 in FIG. 3A. The pump 332 may directly touch the skin 12, but preferably contact between the pump and the skin is minimized such that the pump primarily receives sweat from the wicking component 340. The wicking component 340 may be a tightly woven wicking textile that is so tightly woven that it is not highly compressible. Other suitable materials for the wicking component 340 include, without limitation, a mesh, textile, or other material containing holes or open spaces that are greater than 20%, greater than 50%, or greater than 80% of the total area, in order to reduce the fluidic volume capacity of the wicking component 340. Pump 332 may be, for example, a sponge.

With reference to FIG. 3C, in an embodiment, the wicking component 340 may include more than one component that allows the material to be permanent or semi-permanent (limited reuses) or disposable (one-time use) with respect to the housing 310. For example, a wicking material 340a may be coupled to the housing 310 by an adhesive 340b.

Figure 4:
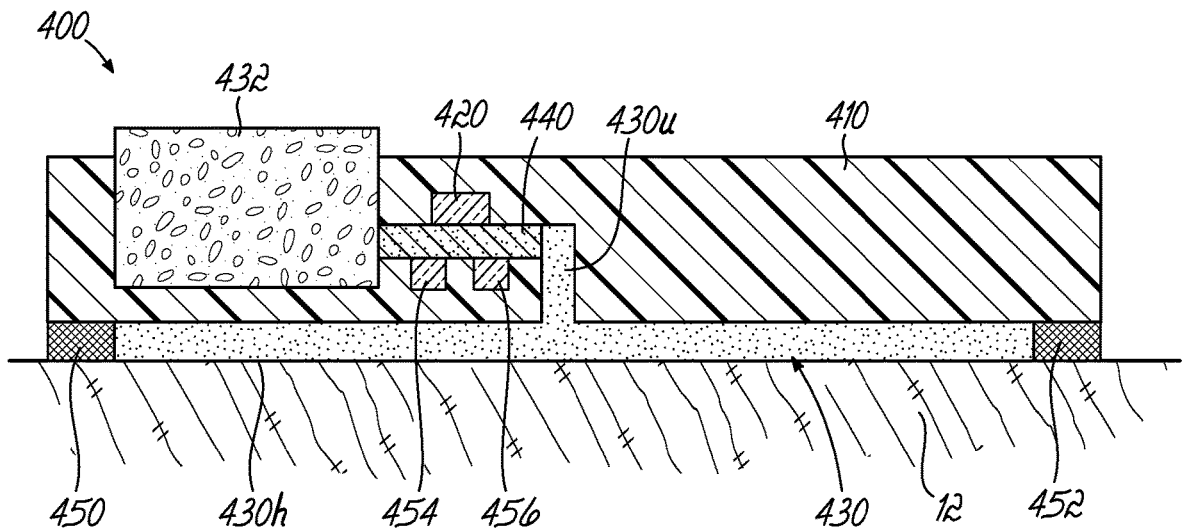
FIG. 4 is a cross-sectional view of at least a portion of a sweat rate measuring device according to an embodiment of the disclosed invention.

FIG. 4 depicts another embodiment of a sweat sensing device 400 capable of measuring sweat rate. In this embodiment, the device 400 includes a housing 410 and a wicking component 440 that is partially disposed in a microfluidic component 430 in fluid communication with a pump 432. As sweat emerges from the skin 12, the sweat travels by positive pressure of sweat generation or by capillary action through the horizontal portion 430h of the component 430, and into the upper portion 430u of the component 430 towards the wicking component 440. Notably, direct contact between the wicking component 440 and the skin 12 is not required to prevent flow reversal of sweat, which supports accurate measurement of the sweat generation rate. The wicking component 440 transports the sweat across a flow rate sensor 420, one or more additional sweat sensors (two sensors 454, 456 are shown), and into the pump 432. Prewetting of the wicking component 440 should occur prior to measuring sweat rate, requiring that the initial flow rate sensor measurements be discarded until the wick saturates. Allowing the wicking component 440 to saturate before recording sweat flow sensor measurements eliminates inaccuracies in flow rate measurements caused by the initial high capillary action of the material of the wicking component 440. While pump 432 is illustrated as being partially exposed, i.e., not fully enclosed in the housing 410, in an alternative embodiment, the pump 432 may be fully enclosed in the housing 410. Leaving at least a portion of the pump 432 exposed would allow for evaporation of water from the pump. One or both of the electrodes 452, 454 may be used to measure sweat conductivity through a counter electrode such as electrode 450.

Figure 5:
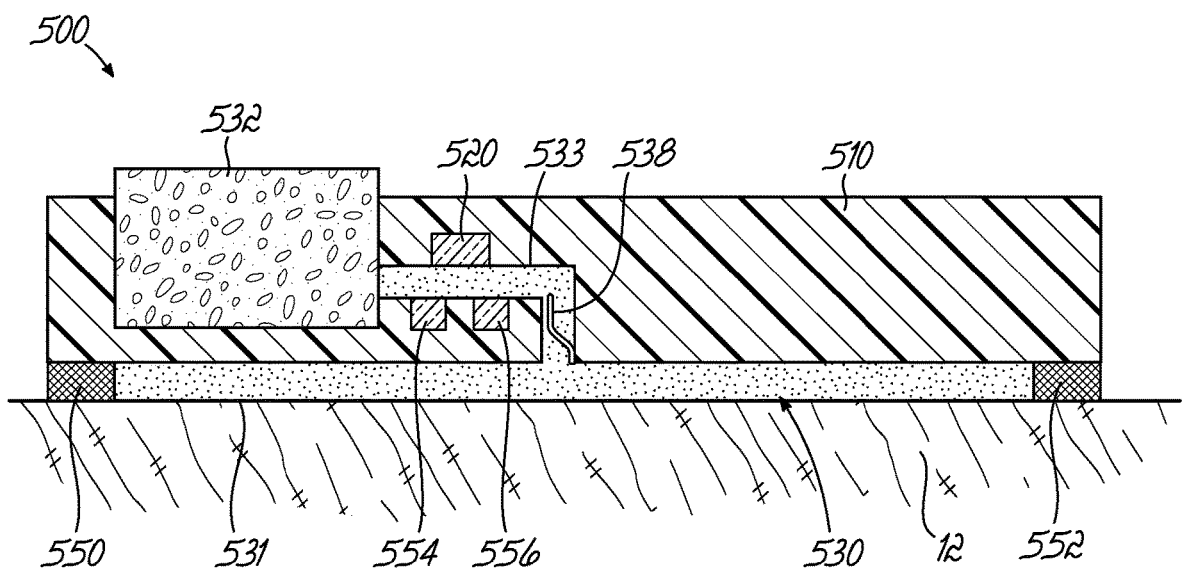
FIG. 5 is a cross-sectional view of at least a portion of a sweat rate measuring device according to an embodiment of the disclosed invention.

With reference to FIG. 5, in an embodiment wherein like numerals refer to like features as shown in FIGS. 2-4, a sweat sensing device 500 for measuring sweat rate includes a housing 510 and a microfluidic component 530. In this embodiment, microfluidic component 530 includes a closed channel 531 in fluid communication with a pump 532. As sweat emerges from the skin 12, the sweat travels through the portion of the channel 531 that is alongside the skin, and progresses into the upper portion of the channel 533. A wicking material is not required, as the sweat progresses through the channel 530 by capillary action and/or positive sweat pressure. The sweat travels through the channel 530, across sensors 520, 554, 556, and into the pump 532, which may be reusable or disposable. In embodiments without a pump, the sweat progresses through channel 530 to an outlet in the housing 510. The sensor 520 may be a flow rate sensor, and the sensors 554, 556 may measure sweat conductivity. Alternatively, one or both of the sensors 554, 556 may be an analyte-specific sensor for measuring characteristics of one or more analytes in sweat. A consistent, unidirectional sweat flow is maintained through the channel 530 and in particular, the upper portion of the channel 531. Unidirectional sweat flow can be maintained by a device requiring a specified pressure for fluid to pass, such as, for example, one or more valve structures 538 in the upper portion of channel 531. Unidirectional sweat flow supports the accurate measurement of sweat rate by reducing or preventing differential fluid pressure effects from motion of the device 500 on skin 12, or the motion of the skin itself, from affecting sweat rate measurements. Valve 538 allows forward flow from the positive pressure of sweat, while preventing backflow of sweat towards the skin, to maintain a constant forward sweat flow across the flow rate sensor 520. A second valve (not shown) can also be located in the channel 530 between the sensor 520 and the pump 532 (or outlet, not shown) to prevent a backflow of sweat towards the flow sensor 520. A number of different types of valving structures can be applicable to the sweat rate measurement devices described herein for preventing backflow in the closed channel. Among these structures are passive valves, including mobile structures (e.g., flaps, membranes, or ball valve) and channel design (e.g., burst valve, or hydrophobic coating); semi-active valves (e.g., ball float, smart materials, check valves); and fully-active valves (e.g., vacuum, rotary pump, piezo, magnetic, or electrically powered membrane, capillary soft valve, bubble). While pump 532 is illustrated as being partially exposed, i.e., not fully enclosed in the housing, in an alternative embodiment, the pump 532 may be fully enclosed in the housing. Leaving at least a portion of the pump 532 exposed would allow for evaporation of water from the pump. One or both of the electrodes 552, 554 may be used to measure sweat conductivity through a counter electrode such as electrode 550.

In closed channel microfluidic sweat sensing devices, noise from a number of different factors can introduce inaccuracies into the sweat rate measurements from a thermal flow sensor. Furthermore, heat dissipates more rapidly from a sweat sample in a closed channel than from a wicking component. This loss of heat can affect the accuracy of measurements by a thermal flow sensor. Accordingly, when using a closed channel device, it is desirable to minimize the channel volume adjacent to the sensor to increase the sensor sensitivity, and also to provide structure for reducing system noise and/or to minimize the effects of noise on the sensor measurements.

Figure 6:
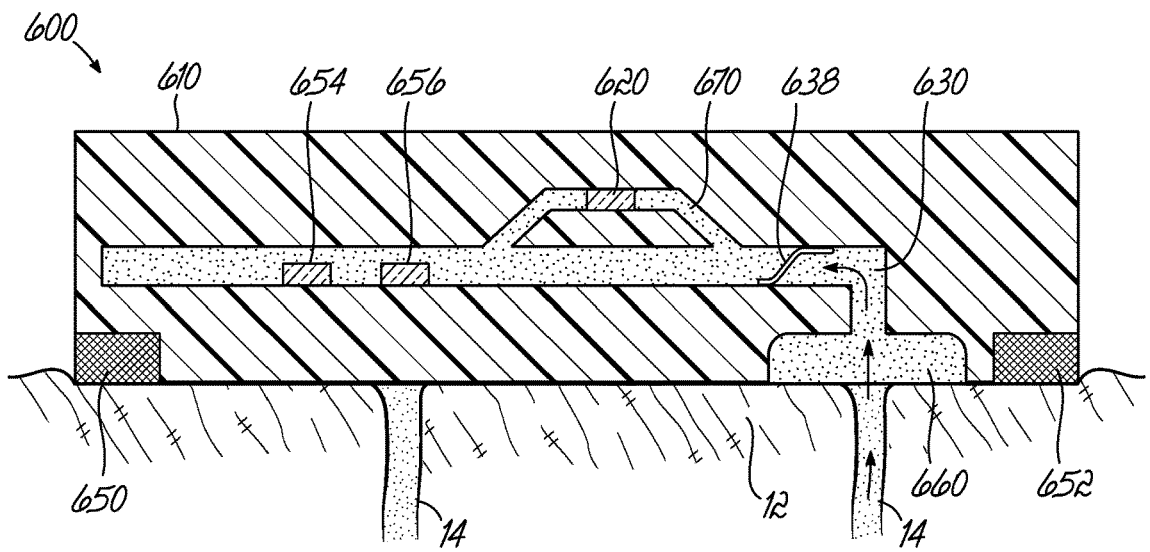
FIG. 6 is a cross-sectional view of at least a portion of a sweat rate measuring device according to an embodiment of the disclosed invention.

FIG. 6 depicts another embodiment of a sweat sensing device 600 capable of measuring sweat rate. In this embodiment, the device 600 includes a housing 610 having a closed channel microfluidic component 630 for conveying sweat from the skin 12 to a flow sensor 620, and one or more sweat sensors (two sensors 654, 656 are depicted). The sweat sensors 654, 656 may measure sweat conductivity or, alternatively, one or more of the sensors may be an analyte-specific sensor. This embodiment features a sweat collector, indicated at 660, that may be located between the device housing 610 and skin 12 for collecting and directing sweat into the channel 630. In the illustrated embodiment, the sweat collector is in the form of a curved funnel that collects sweat from the skin. Similar collectors may be used in other embodiments described herein. As sweat emerges from the skin 12, it travels first into the collector 660, and then progresses into the upper portion of the channel 630. The sweat exiting one or more sweat glands 14 progresses through the channel 630 by capillary action, diffusion, advective transport, or a combination thereof. To increase the sensitivity of the flow sensor 620, a secondary, flow sensing channel 670 branches off from the main sweat flow channel 630 to redirect a reduced volume of sweat to the flow rate sensor 620. The flow sensing channel 670 branches from the main channel 630 at an angle selected to optimize flow sensor measurements without adversely affecting the sweat flow rate to the sweat sensors 654, 656. Flow sensing channel 670 has a width that is less than the main sensing channel 630 to form a volume-reduced pathway past the flow sensor 620, and may approach or be substantially equal to the width of the flow sensor 620. The depth of the flow sensing channel 670 is also minimized to further reduce the channel volume. The reduced volume in flow sensing channel 670 increases the sensitivity of the flow sensor 620 by increasing the sweat flow rate and decreasing the bulk sweat volume flowing past the sensor. Flow sensor 620 is also less affected by noise caused by flow dynamics in the volume-reduced pathway 670. One or more valves 638 can be located in the channel 630 to prevent backflow of sweat in the direction of the skin. One or both of the electrodes 652, 654 may be used to measure sweat conductivity through a counter electrode such as electrode 650.

Figure 7A:
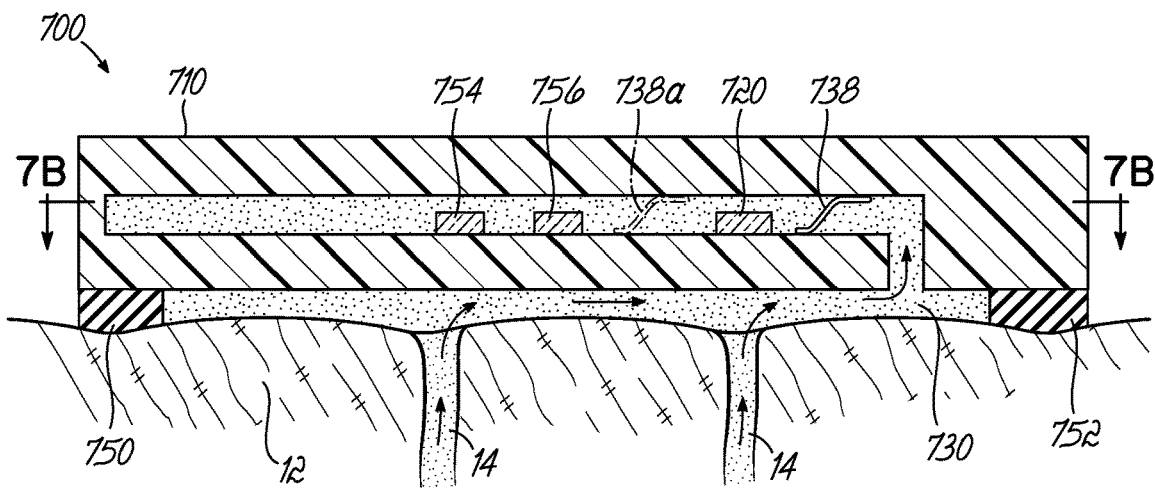
FIG. 7A is a cross-sectional view of at least a portion of a sweat rate measuring device according to an embodiment of the disclosed invention.
Figure 7B:
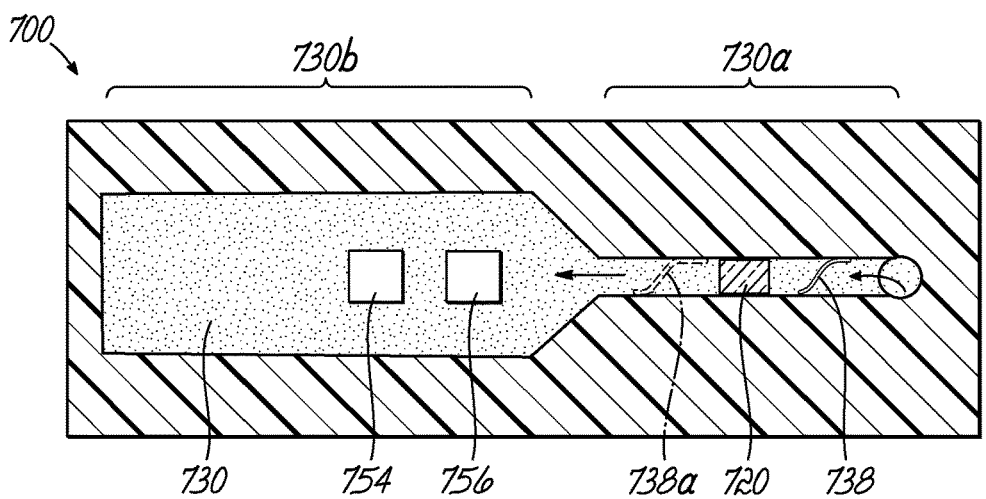
FIG. 7B is a cross-sectional view of the device of FIG. 7A, taken along line 7B-7B in FIG. 7A.

FIGS. 7A and 7B illustrate another embodiment of a closed channel sweat sensing device capable of measuring sweat rate. In this embodiment, the device 700 includes a housing 710 and a closed channel microfluidic component 730, extending from the skin 12 into the housing 710, for conveying sweat to one or more sensors 720, 754, 756. Sweat exiting one or more sweat glands 14 is conveyed through channel 730 by advective transport, capillary action, diffusion, or a combination of these factors. Sensor 720 is a thermal flow sensor or another type of flow rate sensor as described in connection with the previous embodiments. Likewise, sensors 754, 756 comprise sweat sensors such as, for example, analyte-specific sensors for detecting and measuring one or more analytes in a sweat sample. In this embodiment, sweat rate is directly and accurately measured by varying the dimensions of the closed channel 730 between the skin and the sensors. In particular, a reduced-volume pathway 730a is provided adjacent to the flow sensor 720. The reduced-volume pathway 730a has a width that is less than the fluid pathway 730b adjacent to or containing analyte-specific sensors 754, 756. The reduced volume in pathway 730a decreases the bulk fluid volume and increases the velocity of the sweat flow past the flow sensor 720. As shown in FIG. 7B, the width of channel 730a approaches or is substantially equal to the width of the flow sensor 720. The depth of channel 730a may also be minimized to further reduce the channel volume, while maintaining sufficient bulk space in the sensor pathway 730b for analyte-specific sensor functionality. The reduced volume in the channel adjacent the flow sensor 720 increases the sensitivity of the flow sensor, and minimizes the heat dissipation from the sweat. In this embodiment, the sensitivity of the flow rate sensor 720 is increased without the need for an additional channel. At least one valve 738 is located in the channel 730 to prevent backflow of sweat in the direction of the skin. Additional valves, indicated at 738a, may optionally be included in channel 730 between the flow sensor 720 and the analyte-specific sensors 754, 756. An optional collector (similar to the collector 660 shown in FIG. 6) may be located between the housing 710 and skin 12 for collecting and directing sweat into the channel 730. One or both of the electrodes 752, 754 may be used to measure sweat conductivity through a counter electrode such as electrode 750.

Figure 8:
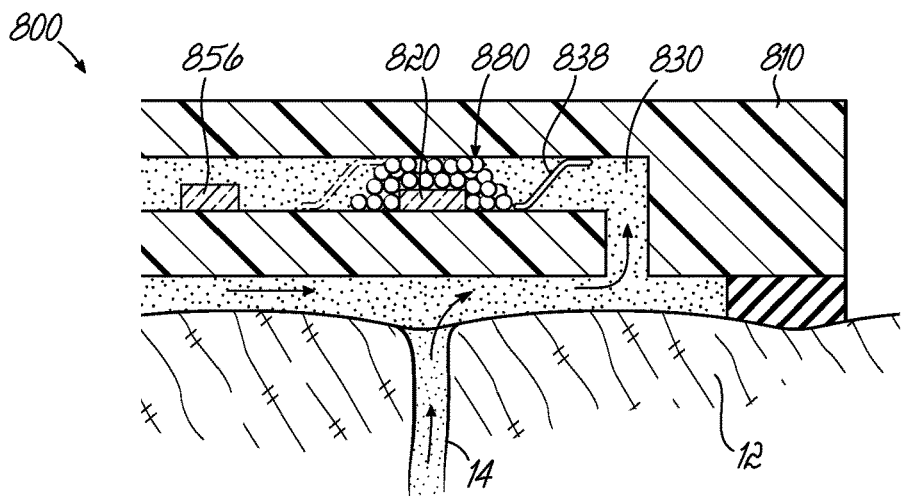
FIG. 8 is a partial cross-sectional view of a portion of a sweat sensing device depicting another embodiment for measuring sweat rate.

With reference to FIG. 8, embodiments of the invention also include a device 800 that includes a housing 810 and a volume reducing component in a closed channel for reducing the sweat volume in contact with a flow sensor 820. Exemplary volume reducing components may include, for example, a plurality of beads 880. The beads 880 can substantially fill the channel 830 around the flow rate sensor 820 while still allowing for fluid contact with the sensor. Beads 880 may be made from various types of materials, both rigid and flexible, with flexible materials allowing the beads to also dampen fluid noise in the channel. Beads 880 comprised of a flexible material may also increase resistance to the sweat flow, and thereby dampen high frequency noise in the device. Additionally, beads 880 may be covered with a functionalized coating to "chemically enhance" the sweat flowing in the channel, including, for example, altering the pH level. The surface of the beads 880 may have a high thermal efficiency to limit the impact of the beads on the temperature of the sweat flow. One or more valves 838 may be located in the channel 830 to prevent backflow of sweat within the channel. Using beads 880, or a similar type of volume reducing component, in channel 830 reduces the effective channel volume surrounding the flow sensor 820, without the need to alter the dimensions of the closed channel. A sensor 856 may measure sweat conductivity or characteristics of one or more analyte in sweat from the one or more sweat glands 14. The volume reducing elements described with respect to FIG. 8 may be utilized with various embodiments of the devices described herein.

Figure 9:
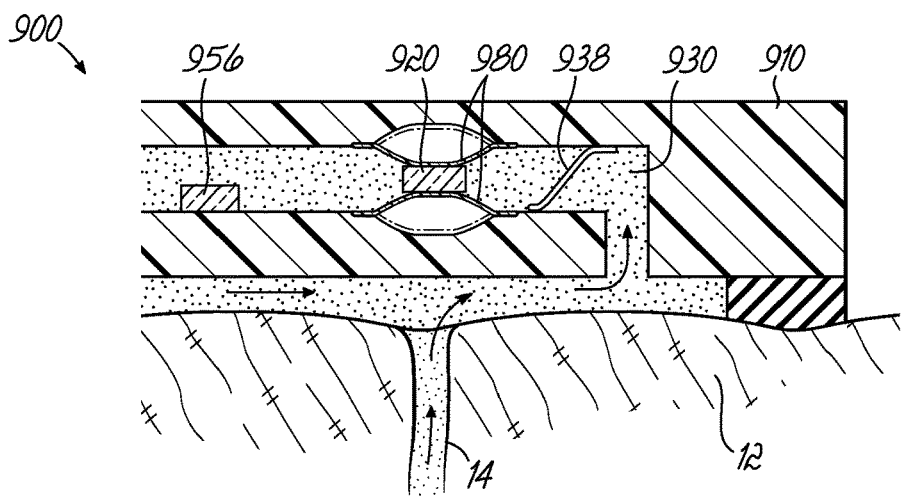
FIG. 9 is a partial cross-sectional view of a portion of a sweat sensing device depicting another embodiment for measuring sweat rate.

With reference to FIG. 9, a sweat sensing device 900 can also include a housing 910 and a microfluidic closed channel 930 having one or more flexible, compressible wall portions 980 adjacent to a flow rate sensor 920. Sweat exiting one or more sweat glands 14 is conveyed through channel 930 by advective transport, capillary action, diffusion, or a combination of these factors. Flexible portions 980 modulate in response to changes in flow dynamics, both from fluid in the channel 930, and from mechanical noise attributable to on-body motion of the sweat sensing device. This modulation reduces the effect of the noise on the flow sensor 920. The flexible channel walls 980 may be made of, for example, a polymer, rubber, silicone or similar material. The location and length of flexible portion 980 in the channel 930 is selected to optimize noise dampening without affecting the functionality of the one or more analyte-specific sensors 956. One or more valves 938 can be located in the channel 930 to prevent backflow of sweat within the channel. A sensor 956 may measure sweat conductivity or characteristics of one or more analyte in sweat from the one or more sweat glands 14. The flexible or compressible wall components described with respect to FIG. 9 may be used in combination with various embodiments of the devices described herein.

Figure 10:
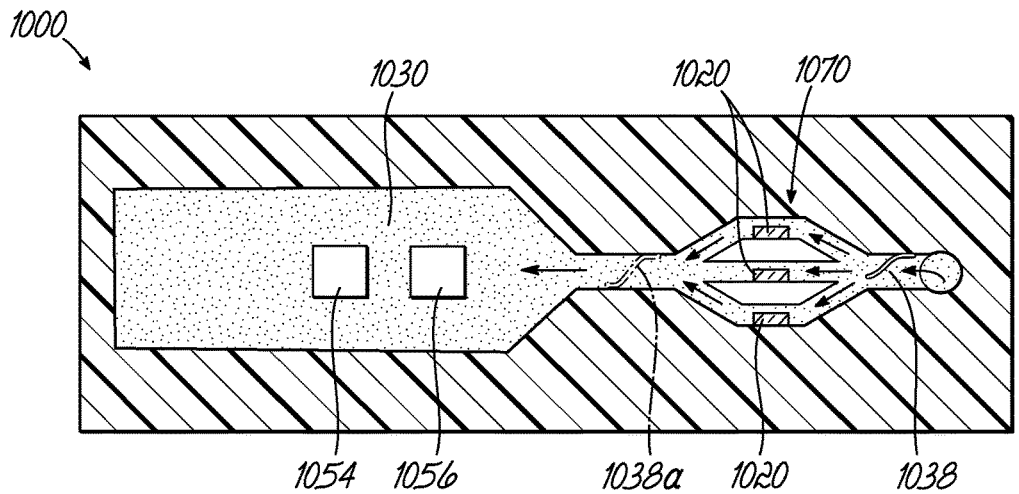
FIG. 10 is a top cross-sectional view of at least a portion of a sweat sensing device depicting another embodiment for measuring sweat rate.

FIG. 10 depicts another embodiment of a sweat sensing device capable of measuring sweat rate. In this embodiment, the device 1000 includes a flow sensing channel network 1070 branching off from the main sweat channel 1030. Each branch of the channel network 1070 forms a reduced-volume pathway adjacent to a separate flow sensor 1020. Each of the flow sensors 1020 has increased sensitivity and is less effected by noise due to the smaller volume of sweat flowing across the sensor. Flow rate measurements from each of the individual flow sensors 1020 may be averaged to provide a more accurate sweat rate measurement with less inaccuracies due to noise. Sweat flow from each branch of the channel network 1070 can be merged in the main channel 1030 prior to reaching the one or more analyte-specific sensors 1054, 1056. The length of the network channels 1070 and merging of the individual sweat flows can be selected to minimize impact on the analyte-specific sensors 1054, 1056 while optimizing flow rate sensing. While three flow sensor channels are shown in FIG. 10, it is envisioned that the number of channels can vary, with the number of channels selected to optimize the flow sensor operation within a particular device.

Figure 11:
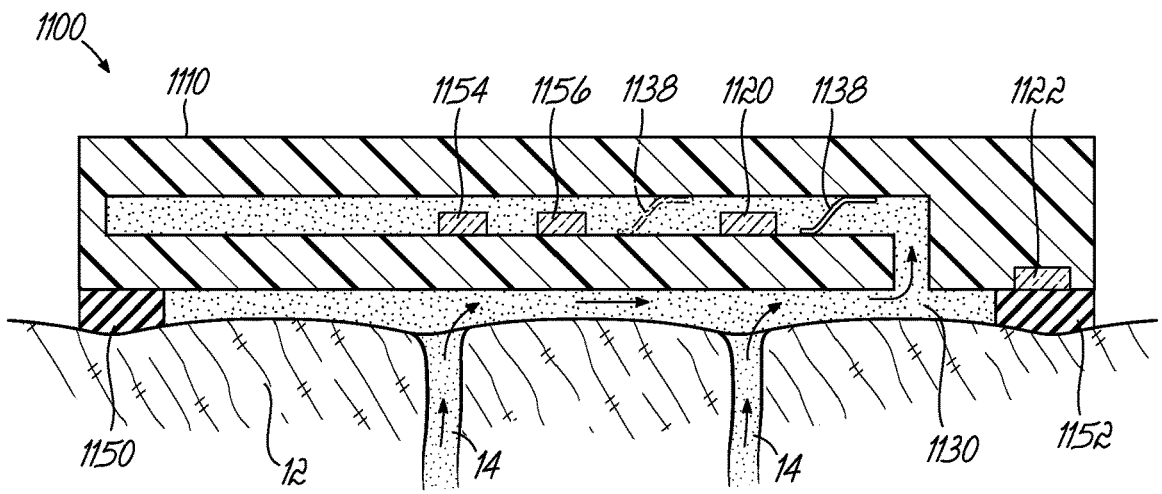
FIG. 11 is a cross-sectional view of at least a portion of a sweat sensing device depicting another embodiment for measuring sweat rate.

FIG. 11 depicts another device 1100 capable of measuring sweat rate in a microfluidic sweat sensing device. In this embodiment, the device 1100 includes a housing 1110 and a flow sensor 1120 that is located in a closed channel 1130 along with optional analyte sensors 1154 and 1156, which may be analyte-specific sensors. Sweat exiting one or more sweat glands 14 is conveyed through channel 730 by advective transport, capillary action, diffusion, or a combination of these factors. The device 1100 also optionally includes one or more valves 1138 upstream and/or downstream of the flow sensor 1120. A second, reference flow sensor 1122 is located in the device 1100 away from contact with the sweat in channel 1130. Reference flow sensor 1122 records system noise unrelated to movement of sweat through channel 1130. The reference sensor measurements can be used in processing the flow sensor measurements to detect and correct for noise cause by flow dynamics within the channel. The reference flow sensor may be used in combination with various embodiments of the devices described herein. One or both of the electrodes 1152, 1154 may be used to measure sweat conductivity through a counter electrode such as electrode 1150.

Figure 12:
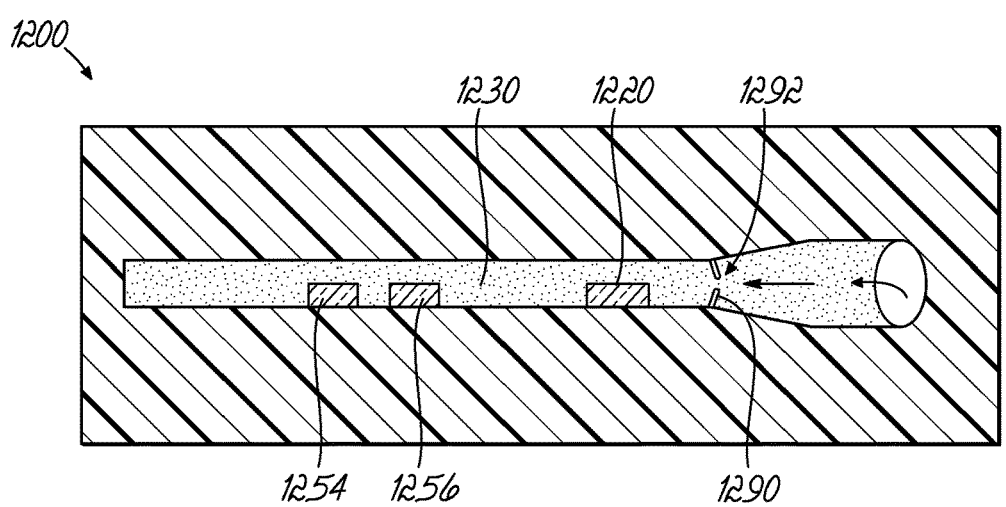
FIG. 12 is a top cross-sectional view of at least a portion of a sweat sensing device depicting another embodiment for measuring sweat rate.

With reference to FIG. 12, another device 1200 is depicted for measuring sweat flow rate in a closed channel. In device 1200, a flow sensor 1220 and one or more analyte sensors 1254, 1256 are located in a closed channel 1230. A flexible diaphragm 1290 spans the diameter of the channel 1230 prior to the flow sensor 1220. Diaphragm 1290 flexes in response to fluid turbulence in the channel 1230 to dampen the turbulence, and thereby reduce the effect of noise on the flow sensor measurements. Diaphragm 1290 includes a fluid passage (thru-hole) for sweat to pass through in the channel 1230 as indicated by arrow 1292. The diaphragm 1290 may be used in combination with various embodiments of the devices described herein.

Figure 13:
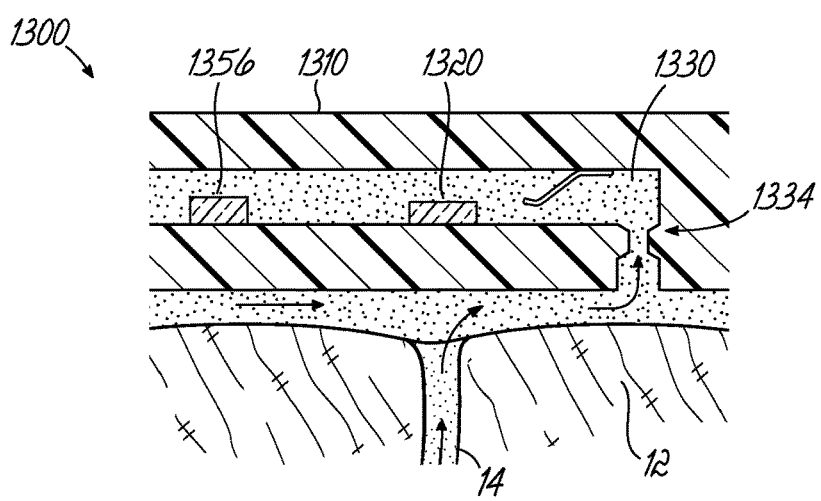
FIG. 13 is a partial cross-sectional view of a portion of a sweat sensing device depicting an embodiment for reducing noise in measuring sweat rate.

FIG. 13 depicts an embodiment for reducing noise in a closed channel sweat rate measurement device 1300 that includes a housing 1310. In this embodiment, a closed channel 1330 has a reduced diameter section, indicated at 1334, adjacent to the channel opening at the skin 12. Sweat exiting one or more sweat glands 14 is conveyed through channel 1330 by advective transport, capillary action, diffusion, or combination of these factors. Sweat flow through the reduced diameter section 1334 creates resistance which combines with the capacitance of the skin to recreate an RC filtering effect for lessening the high frequency noise in the device. The reduced diameter section 1334 may be used in combination with various embodiments of the devices described herein.

Figure 14:
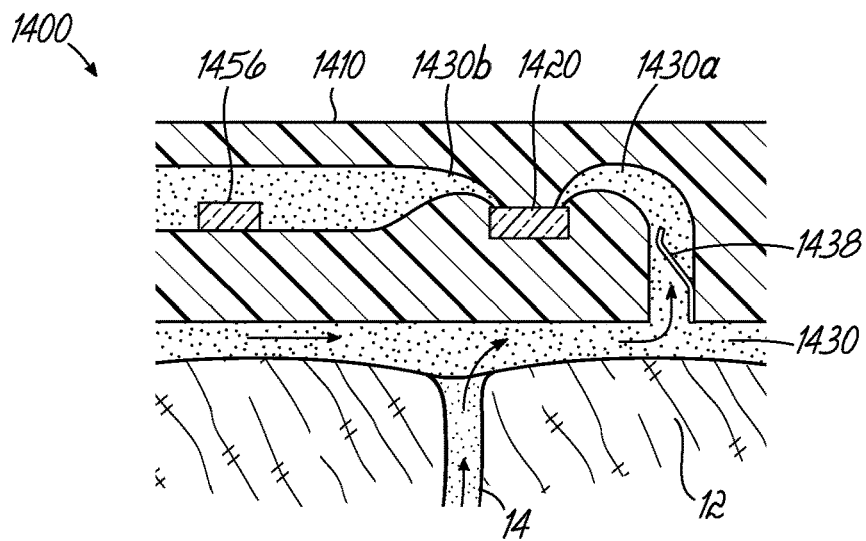
FIG. 14 is a partial cross-sectional view of a portion of a sweat sensing device depicting another embodiment for measuring sweat rate.

With reference to FIG. 14, another device 1400 is depicted for measuring sweat flow rate. Device 1400 includes a housing 1410 and a closed channel 1330. In this device, a thermal flow sensor 1420, such as from Sensirion AG Switzerland, is used for measuring sweat rate. Flexible, narrow channels 1430a and 1430b are connected to input and output ports on the sensor 1420 for directing the sweat flow through the flow sensor 1420. A valve 1438 can prevent sweat backflow in the channel. The flexible narrow channels 1430a and 1430b may be used in combination with the various embodiments of the devices described herein.

Figure 14A:
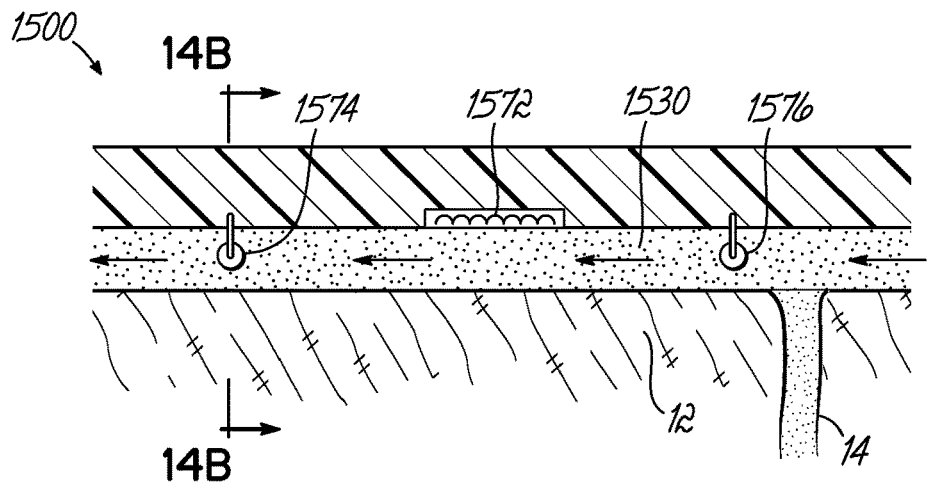
FIG. 14A is a partial perspective, partial side cross-sectional view of a portion of a sweat rate measurement device.
Figure 14B:
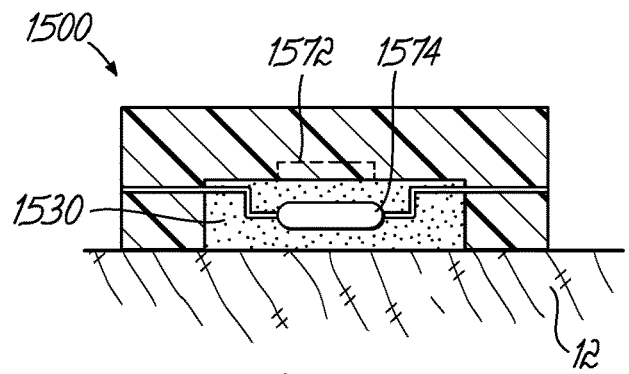
FIG. 14B is a partial perspective, partial side cross-sectional view of a portion of a sweat rate measurement device.

FIGS. 14A and 14B depict another embodiment for a device 1500 capable of measuring sweat rate. In this embodiment, a heater 1572 is attached to a surface of the closed channel 1530. First and second resistive elements 1574, 1576 are separately connected across the channel 1530. The resistive elements are rigidly attached to opposite sides of the channel 1530, and suspended therebetween by pairs of flexible attachment arms. The flexible attachment arms allow the resistive elements 1574, 1576 to flex in response to sweat flow through the channel. The heater 1572 and resistive elements 1574, 1576 form a flow sensor. The flexible nature of the resistive elements dampens the effect of flow dynamics in the channel, thereby reducing the noise recorded by the flow sensor. The elements described with respect to FIGS. 14A and 14B may be used in combination with various embodiments of the devices described herein.

Any of the sweat sensing device embodiments described above may include a plurality of additional components or sensors to improve detection of sweat flow rate and sweat analytes, including a reference electrode, a pH sensor, a temperature sensor, a galvanic skin response sensor, a sweat conductivity sensor, a skin impedance sensor, a capacitive skin proximity sensor, and an accelerometer. The sweat sensing device may also include computing and data storage capability sufficient to operate the device, such as the ability to conduct communication among system components, perform data aggregation, and execute algorithms capable of generating notification messages. The sweat sensing device may have varying degrees of onboard computing capability (i.e., processing and data storage capacity). For example, all computing resources could be located onboard the device, or some computing resources could be located on a disposable portion of the device and additional processing capability located on a reusable portion of the device. Alternatively, the device may rely on portable, fixed, or cloud-based computing resources. In addition to the above, sweat sensing devices and systems as described herein may contain other aspects including, without limitation, an onboard real-time clock, an onboard flash memory (e.g., 1 MB minimum), Bluetooth™ or other communications hardware, a multiplexer to process a plurality of sensor outputs, and additional supporting technology or features which are not captured in the description herein, but would be otherwise known to those skilled in the art.

In each of the embodiments, the channel volume is chosen based on the requirements of the application. The channel cross-section may be small enough to facilitate capillary action that will at least partially draw the sweat sample through the channel. Other embodiments will rely on positive pressure from sweat generation to drive the sample though the channel. Some embodiments will include air traps or air bubble venting components to prevent air bubbles from interfering with measurements taken by a flow sensor, electrodes or other sensors. In the wicking component embodiments, the wicking material may be prewet with fluid prior to initiating sweat rate measurements. In the closed channel embodiments, the channel may be pre-filled with fluid prior to activation in order to accelerate the time period when sweat sensing may begin, thereby limiting the need to fill the sensing device with sweat prior to initiating sweat measurements. Additionally, electromagnetic shielding is preferably provided within the device to protect the flow sensor measurements from inaccuracies due to the placement on the wearer's skin or interference from other electronics.

Furthermore, while the depicted embodiments have shown specific numbers of sensors, it should be understood that the number of sensors may vary depending on the application. Although not described in detail herein, other essential steps which are readily interpreted from or incorporated along with the disclosed embodiments shall be included as part of the invention. The embodiments that have been described herein provide specific examples to portray inventive steps, but will not necessarily cover all possible embodiments commonly known to those skilled in the art.

What is claimed is:

1. A sweat sensing device capable of directly measuring sweat flow rate comprising:
   at least one flow rate sensor for measuring a sweat flow rate;
   at least one analyte sensor for measuring a characteristic of an analyte in sweat; and a microfluidic component comprising a fluid pathway for conveying at least one sweat sample into fluid communication with the at least one flow rate sensor, the at least one analyte sensor, or both the at least one flow rate sensor and the at least one analyte sensor, wherein the pathway has a first portion for collecting a sample and a second portion adjacent to the at least one flow rate sensor and the at least one analyte sensor, wherein the second portion has a volume-reduced pathway relative to the first portion;

wherein the second portion of the fluid pathway comprises a first valve and a second valve, wherein the first valve is positioned in a portion of the fluid pathway preceding the flow rate sensor, and wherein the second valve is positioned in a portion of the fluid pathway following the flow rate sensor.

2. The device of claim 1, wherein the at least one flow rate sensor includes a thermal flow rate sensor.

3. The device of claim 2, wherein the microfluidic component comprises a closed channel.

4. The device of claim 3, wherein at least one of the first valve and the second valve is positioned in the closed channel for maintaining a unidirectional flow of sweat across the at least one flow rate sensor.

5. The device of claim 1, wherein the microfluidic component includes a wicking material in contact with the at least one flow rate sensor.

6. The device of claim 5, wherein the wicking material is configured to be fully wetted during sensing.

7. The device of claim 1, wherein a flow of sweat across the at least one flow rate sensor is unidirectional.

8. The device of claim 1, wherein the microfluidic component further comprises a pump.

9. The device of claim 8, wherein the pump transports sweat across at least one of the at least one flow rate sensor and the at least one analyte sensor.

10. The device of claim 8, wherein the pump is a wicking component.

11. The device of claim 8, wherein the pump has a capacity that is greater than 1 µL.

12. The device of claim 8, wherein the pump has a capacity that is greater than 1 mL.

13. The device of claim 1, configured to detect flow reversal.

14. The device of claim 13, comprising software that detects changes in flow rate, and determines flow rate reversal based on the detected changes in flow rate.

15. The device of claim 1, wherein at least a portion of the microfluidic component is capable of being replaced.

16. The device of claim 1, wherein the device includes a housing and the microfluidic component is in the housing, wherein the microfluidic component includes a first wicking material configured to bring sweat into contact with the at least one flow rate sensor and the at least analyte sensor and a pump in fluid communication with the first wicking material.

17. The device of claim 16, wherein the housing further includes a latch to allow for removal and replacement of at least one of the first wicking material and the pump.

18. The device of claim 16, wherein the pump is comprised of a second wicking material.

19. The device of claim 18, wherein the wicking capacity of the pump is greater than the wicking capacity of the first wicking material.

* * * * *